(12) United States Patent
Sheldon et al.

(10) Patent No.: US 8,682,433 B2
(45) Date of Patent: Mar. 25, 2014

(54) METHOD FOR EFFICIENT DELIVERY OF DUAL SITE PACING

(75) Inventors: Todd J. Sheldon, North Oaks, MN (US); Vincent E. Splett, Apple Valley, MN (US); Robert W. Stadler, Shoreview, MN (US); Wade M. Demmer, Coon Rapids, MN (US)

(73) Assignee: Medtronic, Inc., Minneapolis, MN (US)

( * ) Notice: Subject to any disclaimer, the term of this patent is extended or adjusted under 35 U.S.C. 154(b) by 98 days.

(21) Appl. No.: 13/301,113

(22) Filed: Nov. 21, 2011

(65) Prior Publication Data

US 2013/0131749 A1 May 23, 2013

(51) Int. Cl.
A61N 1/368 (2006.01)
(52) U.S. Cl.
USPC .......................................................... 607/17
(58) Field of Classification Search
USPC .......................................................... 607/17
See application file for complete search history.

(56) References Cited

U.S. PATENT DOCUMENTS

| | | | |
|---|---|---|---|
| 5,117,824 A | 6/1992 | Keimel | |
| 5,707,398 A | 1/1998 | Lu | |
| 5,873,898 A | 2/1999 | Hemming | |
| 6,332,096 B1 | 12/2001 | Mower | |
| 6,393,316 B1 | 5/2002 | Gillberg | |
| 6,477,417 B1 | 11/2002 | Levine | |
| 6,611,712 B2 | 8/2003 | Spinelli | |
| 6,687,545 B1 | 2/2004 | Lu | |
| 6,704,598 B2 | 3/2004 | Ding | |
| 6,950,701 B2 | 9/2005 | Begemann | |
| 7,123,963 B2 | 10/2006 | Sawchuk | |
| 7,239,913 B2 | 7/2007 | Ding | |
| 7,555,336 B2 | 6/2009 | Sheth | |
| 7,697,977 B2 | 4/2010 | Yonce | |
| 2003/0083709 A1* | 5/2003 | Zhu et al. ........................ 607/27 |
| 2004/0172079 A1 | 9/2004 | Chinchoy | |
| 2008/0177344 A1 | 7/2008 | Maskara | |
| 2009/0030470 A1 | 1/2009 | Holmstrom | |
| 2009/0043352 A1 | 2/2009 | Brooke | |
| 2009/0240298 A1 | 9/2009 | Lian | |
| 2010/0121396 A1 | 5/2010 | Gill | |
| 2010/0121404 A1 | 5/2010 | Bjorling | |
| 2010/0137935 A1 | 6/2010 | Parikh | |
| 2010/0262204 A1 | 10/2010 | McCabe | |
| 2010/0331906 A1 | 12/2010 | Williamson | |

OTHER PUBLICATIONS

Dendy KF, et al.; "Anodal stimulation: An underrecognized cause of nonresponders to cardiac resynchronization therapy"; Indian Pacing and Electrophysiology Journal, 2011, 11(3):pp. 64-72.

\* cited by examiner

*Primary Examiner* — Eric D. Bertram
(74) *Attorney, Agent, or Firm* — Michael C. Soldner

(57) ABSTRACT

An implantable device and associated method for delivering a multi-site pacing therapy includes electrodes for sensing cardiac signals and delivering cardiac pacing pulses. Electrodes positioned at first and second selected pacing sites are used to deliver pacing pulses to a first heart chamber using a bipole comprising the first electrode and the second electrode. A controller is configured to determine if anodal and cathodal capture can be achieved during pacing using the bipole. Responsive to anodal and cathodal capture being achieved, the controller selects a multi-site pacing configuration comprising the bipole for singly pacing the first and second pacing sites.

21 Claims, 6 Drawing Sheets

METHOD FOR EFFICIENT DELIVERY OF DUAL SITE PACING

FIELD OF THE DISCLOSURE

The disclosure relates generally to medical devices for delivering electrical stimulation and, in particular, to an apparatus and method for dual site pacing in the heart.

BACKGROUND

Cardiac resynchronization therapy (CRT) is a treatment for heart failure patients in which one or more heart chambers are electrically stimulated (paced) to restore or improve heart chamber synchrony. Achieving a positive clinical benefit from CRT depends in part on the location of the pacing site, particularly in the left ventricle (LV). Thus, placement of the pacing leads and selecting electrode pacing sites is important in promoting a positive outcome from CRT. As multi-polar cardiac pacing leads become commercially available, multi-site pacing in a given heart chamber is possible, potentially achieving greater restoration of heart chamber synchrony and therapeutic benefit. However, delivering pacing at multiple pacing sites will generally be at a cost of greater energy requirements and faster depletion of the pacing device battery. A need remains for methods and apparatus for optimizing the delivery of multi-site pacing in terms of both energy efficiency and therapeutic benefit.

DETAILED DESCRIPTION

Figure 1:
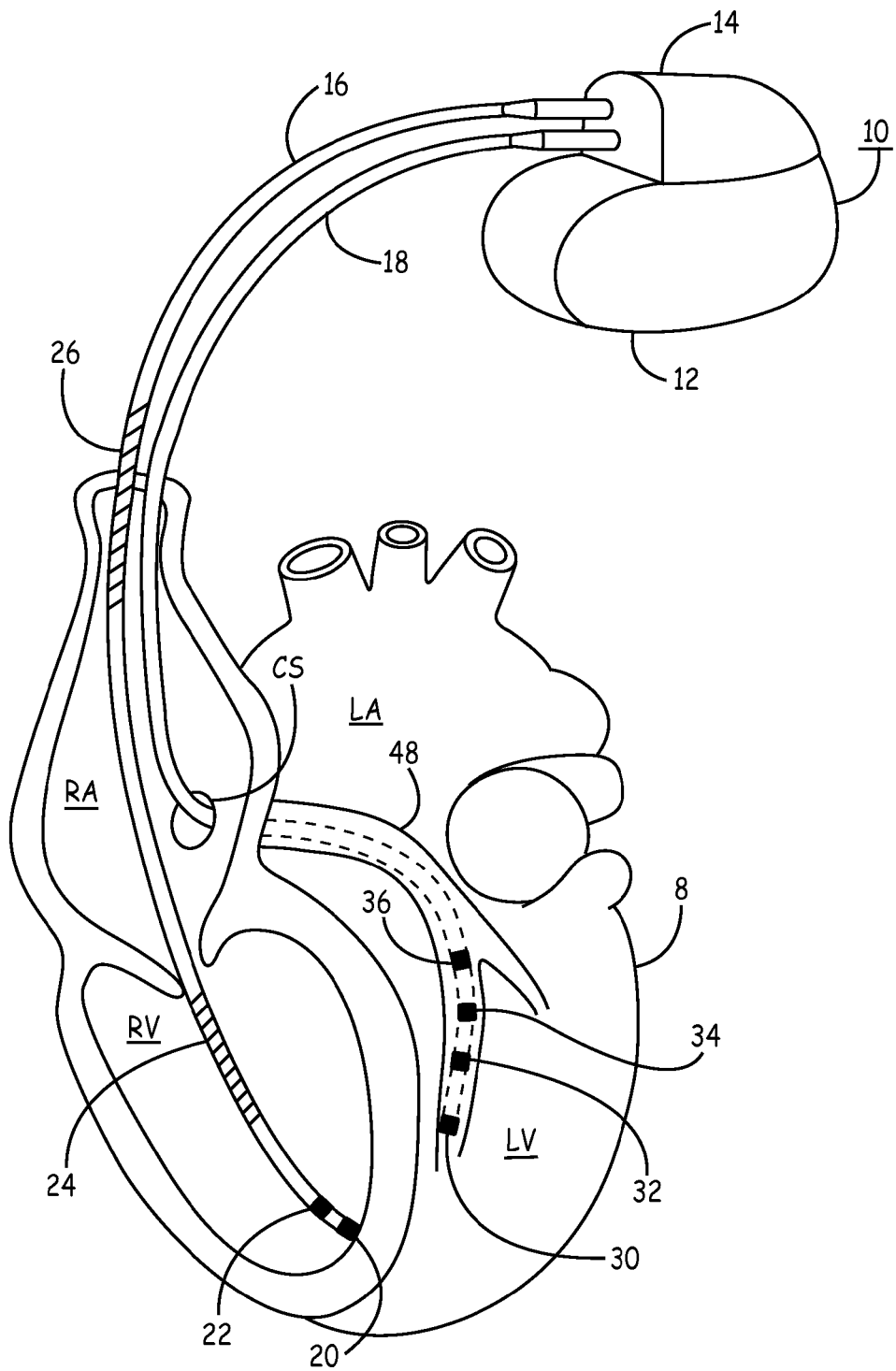
FIG. 1 depicts an implantable medical device (IMD) coupled to a patient's heart.

In the following description, references are made to illustrative embodiments. It is understood that other embodiments may be utilized without departing from the scope of the disclosure. As used herein, the term "module" refers to an application specific integrated circuit (ASIC), an electronic circuit, a processor (shared, dedicated, or group) and memory that execute one or more software or firmware programs, a combinational logic circuit, or other suitable components that provide the described functionality.

Methods and associated circuitry are described herein for selecting multiple pacing sites along a heart chamber for delivering a pacing therapy such as CRT. In some embodiments, the methods include determining optimal pacing sites based on measurements of left ventricular activation times or other measurements correlated to cardiac hemodynamic functions. Additionally or alternatively, the methods include detecting anodal stimulation during bipolar stimulation of a heart chamber for use in achieving dual site pacing using a single pair of electrodes. These methods may be implemented in any single, dual, or multi-chamber pacing device having at least two electrodes positioned for bipolar pacing of a heart chamber. More often, practice of the disclosed methods will be used when multiple electrodes are available along a paced heart chamber providing two or more bipolar electrode vectors to choose from for pacing the heart chamber.

In some embodiments, at least one electrode positioned away from the heart chamber is provided for use as an anode for obtaining measurements during unipolar pacing of the heart chamber that are used for discriminating between anodal and cathodal capture. The anode electrode may be in or along another heart chamber, along the housing of an associated IMD, or a subcutaneously implanted electrode such as a patch electrode. In some embodiments used for detecting anodal capture, which involve measuring conduction times between heart chambers, electrodes for sensing a conducted depolarization in a heart chamber other than the one being paced are needed. In other embodiments, a distant sensing bipole may be used to measure a conduction time within the same chamber being paced.

In the following description, a dual-chamber (biventricular) pacing device is described as one illustrative embodiment of a device that may utilize the multi-site pacing methods described herein. This device is used in particular for delivering CRT by pacing in one or both ventricles. It should be recognized, however, that multi-site pacing may be implemented in numerous device configurations that include at least bipolar pacing capabilities in one or more heart chambers for delivering CRT or any other pacing therapy. Furthermore, aspects of the multi-site electrical stimulation methods may be implemented in any medical device delivering electrical stimulation to excitable body tissue and are not necessarily limited to practice in cardiac pacing applications.

FIG. 1 depicts an implantable medical device (IMD) 10 coupled to a patient's heart 8 by way of a right ventricular (RV) lead 16 and a coronary sinus (CS) lead 18. The IMD 10 is embodied as a cardiac pacing device provided for restoring ventricular synchrony by delivering pacing pulses to one or both ventricles as needed to control the heart activation sequence. The heart 8 is shown in a partially cut-away view illustrating the upper heart chambers, the right atrium (RA) and left atrium (LA), and the lower heart chambers, the right ventricle (RV) and left ventricle (LV), and the great cardiac vein 48, which branches to form inferior cardiac veins. The great cardiac vein 48 opens into the coronary sinus (CS) in the right atrium.

The transvenous leads 16 and 18 connect IMD 10 with the RV and the LV, respectively. It is recognized that in some embodiments, additional leads and/or electrodes may be coupled to an IMD for connecting the IMD with the RA and the LA to provide sensing and/or pacing in three or all four chambers of the heart.

Each lead 16 and 18 carries pace/sense electrodes coupled to insulated, elongated conductors extending through leads 16 and 18. A remote indifferent housing electrode 12 is formed as part of the outer surface of the housing of the IMD 10. The pace/sense electrodes and the remote indifferent housing electrode 12 can be selectively employed to provide a number of unipolar and bipolar pace/sense electrode combinations for pacing and sensing functions.

RV lead 16 is shown as a transvenous, endocardial lead passed through the RA into the RV. The RV lead 16 is formed with a proximal lead connector adapted for insertion into a connector bore of IMD connector block 14. The lead connector (not shown in FIG. 1) electrically couples electrodes 20, 22, 24, and 26 carried by RV lead 16 to internal circuitry of IMD 10 via connector block 14. RV pace/sense tip electrode 20 and proximal RV pace/sense ring electrode 22 are provided for RV pacing and sensing of RV EGM signals. RV lead 16 additionally carries an RV coil electrode 24 and a superior vena cava (SVC) coil electrode 26, which may be used for delivering high-voltage cardioversion or defibrillation shocks. RV ring electrode 22, RV coil electrode 24 or SVC coil electrode 26 are used in some embodiments as an anode paired with an electrode positioned along the LV for delivering unipolar pacing pulses in the LV during anodal capture analysis.

In the illustrative embodiment, a multi-polar LV CS lead 18 is passed through the RA, into the CS and further into a cardiac vein 48 to extend the distal four pace/sense electrodes 30, 32, 34 and 36 along the LV chamber to achieve LV pacing and sensing of LV EGM signals using any combination of electrodes 30 through 36. The LV CS lead 18 is coupled at a proximal end lead connector (not shown) inserted into a bore of IMD connector block 14 to provide electrical coupling of electrodes 30 through 36 to IMD internal circuitry. In other embodiments, the multi-polar lead 18 may include more than four electrodes or fewer than four electrodes.

In alternative embodiments pace/sense electrodes may be operatively positioned along the LV for pacing the LV myocardium using multiple LV leads advanced into different cardiac veins, using endocardial leads and electrodes, epicardial leads and electrodes, or any combination thereof. As used herein, pacing a heart chamber using an electrode positioned "along a heart chamber" refers to pacing the myocardial tissue of the heart chamber to capture that heart chamber, and includes using electrodes operatively positioned at endocardial, epicardial, or intravenous locations or any combination thereof.

The depicted positions of the leads and electrodes shown in FIG. 1 in or about the right and left ventricles are approximate and merely illustrative. It is recognized that alternative leads and pace/sense electrodes that are adapted for placement at pacing or sensing sites on or in or relative to the RA, LA, RV and/or LV may be used in conjunction with the methods described herein. For example, in a three chamber pacing device, a RA lead may be positioned carrying a tip and ring electrode for pacing and sensing in the right atrial chamber. Additionally, in a four chamber embodiment, LV CS lead 22 could bear proximal LA CS pace/sense electrode(s) positioned along the lead body to lie adjacent the LA for use in pacing the LA or sensing LA EGM signals. A multi-chamber device in which methods described herein may be implemented is generally disclosed in U.S. Pat. No. 7,555,336 (Sheth, et al.), hereby incorporated herein by reference in its entirety.

The electrodes designated above as "pace/sense" electrodes can generally be used for both pacing and sensing functions. These "pace/sense" electrodes can be selected to be used exclusively as pace or sense electrodes or to be used for both pacing and sensing in programmed combinations for sensing cardiac signals and delivering cardiac stimulation pulses along selected sensing and pacing vectors. Separate or shared indifferent pace and sense electrodes can also be designated in pacing and sensing functions, including the use of RV coil electrode 24 and/or SVC coil electrode 26 as a pacing anode or used for sensing cardiac signals.

Figure 2:
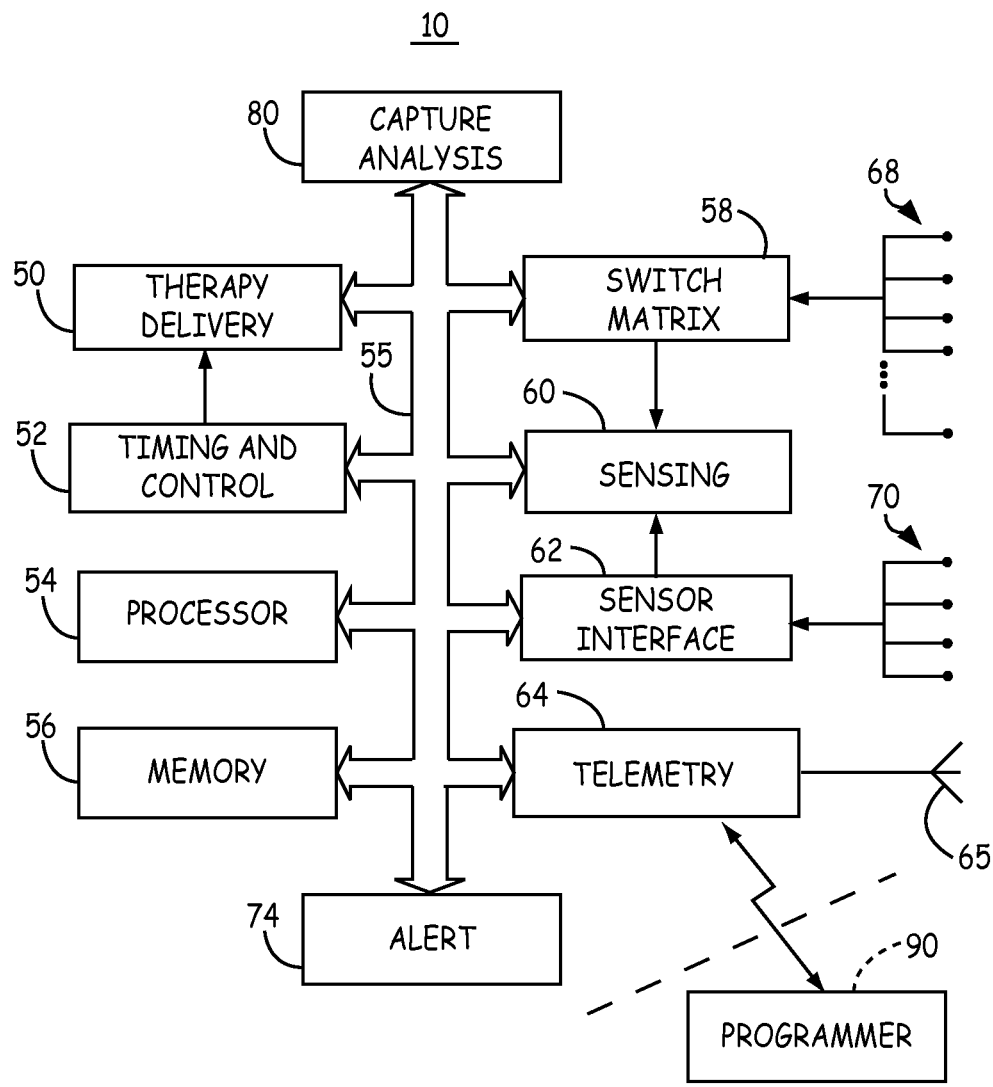
FIG. 2 is a functional block diagram of the IMD shown in FIG. 1.

FIG. 2 is a functional block diagram of IMD 10. IMD 10 generally includes timing and control circuitry 52 and an operating system that may employ processor 54 for controlling sensing and therapy delivery functions in accordance with a programmed operating mode. Processor 54 and associated memory 56 are coupled to the various components of IMD 10 via a data/address bus 55. Processor 54, memory 56, timing and control 52, and capture analysis module 80 may operate cooperatively as a controller for executing and controlling various functions of IMD 10.

Processor 54 may include any one or more of a microprocessor, a controller, a digital state machine, a digital signal processor (DSP), an application specific integrated circuit (ASIC), a field-programmable gate array (FPGA), or equivalent discrete or integrated logic circuitry. In some examples, processor 54 may include multiple components, such as any combination of one or more microprocessors, one or more controllers, one or more DSPs, one or more ASICs, or one or more FPGAs, as well as other discrete or integrated logic circuitry. The functions attributed to processor 54 herein may be embodied as software, firmware, hardware or any combination thereof. In one example, capture analysis module 80 and/or sensing module 60 may, at least in part, be stored or encoded as instructions in memory 56 that are executed by processor 54.

IMD 10 includes therapy delivery module 50 for delivering a therapy in response to determining a need for therapy based on sensed physiological signals. Therapy delivery module 50 includes a signal generator for providing electrical stimulation therapies, such as cardiac pacing or arrhythmia therapies, including CRT. Therapies are delivered by module 50 under the control of timing and control 52. Therapy delivery module 50 is coupled to two or more electrodes 68 via a switch matrix 58 for delivering pacing pulses to the heart. Switch matrix 58 may be used for selecting which electrodes and corresponding polarities are used for delivering electrical stimulation pulses. Electrodes 68 may correspond to the electrodes 12, 20, 22, 24, 26, 30, 32, 34, and 36 shown in FIG. 1 or any electrodes coupled to IMD 10.

Timing and control 52, in cooperation with processor 54 and capture analysis module 80, control the delivery of pacing pulses by therapy delivery 50 according to a programmed therapy protocol, which includes the option of multi-site pacing wherein multiple pacing sites along a heart chamber are selected using methods described herein. Selection of multiple pacing sites and control of the pacing therapy delivered may be based on results of activation time measurements or an anodal capture analysis algorithm or a combination of both. For example, the detection of anodal capture may be used to select which of electrodes 30 through 36 and corresponding polarities are used in delivering a cardiac pacing therapy. As such, capture analysis module 80 is configured to determine pacing capture thresholds and detect the presence of anodal capture for determining both anodal and cathodal capture thresholds for a given pacing vector in some embodiments.

Electrodes 68 are also used for receiving cardiac electrical signals. Cardiac electrical signals may be monitored for use in diagnosing or monitoring a patient condition or may be used for determining when a therapy is needed and in controlling the timing and delivery of the therapy. When used for sensing, electrodes 68 are coupled to sensing module 60 via switch matrix 58. Sensing module 60 includes sense amplifiers and may include other signal conditioning circuitry and an analog-to-digital converter. Cardiac EGM signals (either analog sensed event signals or digitized signals or both) may then be used by processor 54 for detecting physiological events, such as detecting and discriminating cardiac arrhythmias, determining activation patterns of the patient's heart, measuring myocardial conduction time intervals, and in performing anodal capture analysis and pacing capture threshold measurements as will be further described herein.

IMD 10 may additionally be coupled to one or more physiological sensors 70. Physiological sensors 70 may include pressure sensors, accelerometers, flow sensors, blood chemistry sensors, activity sensors or other physiological sensors for use with implantable devices. Physiological sensors may be carried by leads extending from IMD 10 or incorporated in or on the IMD housing. Sensor interface 62 receives signals from sensors 70 and provides sensor signals to sensing module 60. In other embodiments, wireless sensors may be implanted remotely from IMD and communicate wirelessly with IMD 10. IMD telemetry circuitry 64 may receive sensed signals transmitted from wireless sensors. Sensor signals are used by processor 54 for detecting physiological events or conditions.

The operating system includes associated memory 56 for storing a variety of programmed-in operating mode and parameter values that are used by processor 54. The memory 56 may also be used for storing data compiled from sensed signals and/or relating to device operating history for telemetry out upon receipt of a retrieval or interrogation instruction. The processor 54 in cooperation with therapy delivery module 50, sensing module 60 and memory 56 executes an algorithm for measuring activation times for selecting pacing sites for delivering multi-site pacing.

A capture analysis algorithm may be stored in memory 56 and executed by processor 54 and/or capture analysis module 80 with input received from electrodes 68 for detecting anodal capture and for measuring pacing capture thresholds. Microprocessor 54 may respond to capture analysis data by altering electrode selection for delivering a cardiac pacing therapy. Data relating to capture analysis may be stored in memory 56 for retrieval and review by a clinician and that information may be used in programming a pacing therapy in IMD 10.

IMD 10 further includes telemetry circuitry 64 and antenna 65. Programming commands or data are transmitted during uplink or downlink telemetry between IMD telemetry circuitry 64 and external telemetry circuitry included in programmer 90.

Programmer 90 may be a handheld device or a microprocessor based home monitor or bedside programming device used by a clinician, nurse, technician or other user. IMD 10 and programmer 90 communicate via wireless communication. Examples of communication techniques may include low frequency or radiofrequency (RF) telemetry using Bluetooth or MICS but other techniques may also be used.

A user, such as a physician, technician, or other clinician, may interact with programmer 90 to communicate with IMD 10. For example, the user may interact with programmer 90 to retrieve physiological or diagnostic information from IMD 10. Programmer 90 may receive data from IMD 10 for use in electrode selection for CRT, particularly data regarding cathodal and anodal capture thresholds and other measurements used in electrode selection such as hemodynamic measurements and LV activation times. A user may also interact with programmer 90 to program IMD 10, e.g., select values for operational parameters of the IMD. For example, a user interacting with programmer 90 may select programmable parameters controlling a cardiac rhythm management therapy delivered to the patient's heart 8 via any of electrodes 68.

Processor 54, or a processor included in programmer 90, is configured to compute battery expenditure estimates in some embodiments. Using measured pacing capture thresholds and lead impedance measurements, along with other measured or estimated parameters, the predicted battery longevity of the IMD 10 may be computed for different pacing configurations. This information may be used in selecting or recommending a multi-site pacing configuration. As such, IMD 10 is configured to perform lead impedance measurements and determine other parameters required for estimated energy expenditure calculations, which may include but are not limited to a history of pacing frequency, capture thresholds, lead impedances, and remaining battery life.

While not shown explicitly in FIG. 2, it is contemplated that a user may interact with programmer 90 remotely via a communications network by sending and receiving interrogation and programming commands via the communications network. Programmer 90 may be coupled to a communications network to enable a clinician using a computer to access data received by programmer 90 from IMD 10 and to transfer programming instructions to IMD 10 via programmer 90.

Reference is made to commonly-assigned U.S. Pat. Nos. 6,599,250 (Webb et al.), 6,442,433 (Linberg et al.) 6,622,045 (Snell et al.), 6,418,346 (Nelson et al.), and 6,480,745 (Nelson et al.) for general descriptions and examples of network communication systems for use with implantable medical devices for remote patient monitoring and device programming, hereby incorporated herein by reference in their entirety.

Figure 3:
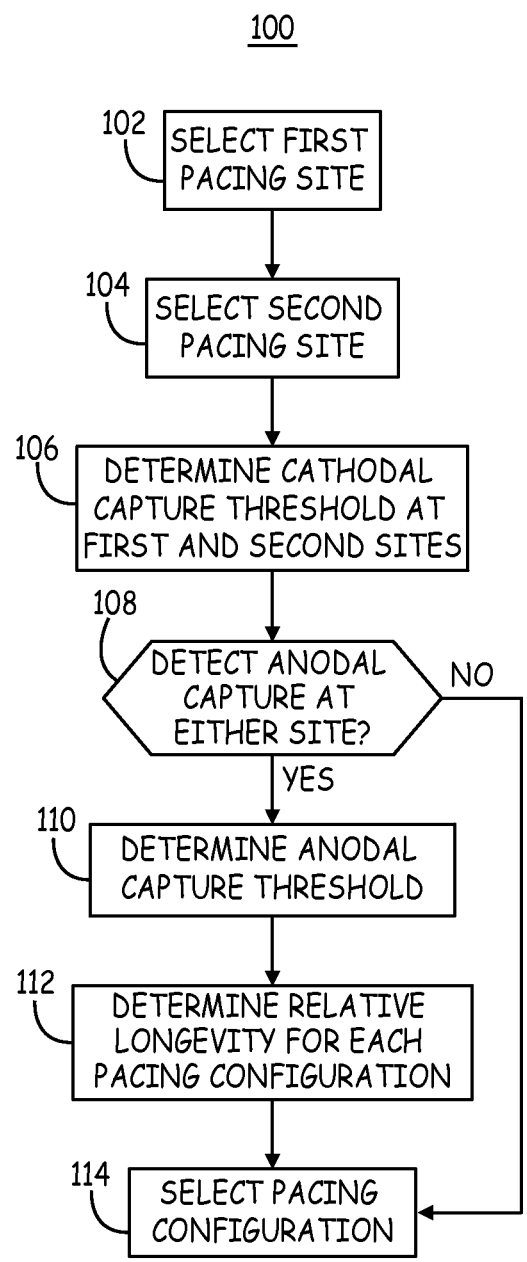
FIG. 3 is a flow chart of a method for selecting electrodes for delivering a multi-site pacing therapy.

FIG. 3 is a flow chart 100 of a method for selecting electrodes for delivering a pacing therapy based at least in part on the detection of anodal capture. Flow chart 100 and other flow charts presented herein are intended to illustrate the functional operation of the device, and should not be construed as reflective of a specific form of software or hardware necessary to practice the methods described. It is believed that the particular form of software, hardware and/or firmware will be determined primarily by the particular system architecture employed in the device and by the particular detection and therapy delivery methodologies employed by the device. Providing circuitry to accomplish the described functionality in the context of any modern IMD, given the disclosure herein, is within the abilities of one of skill in the art.

Methods described in conjunction with flow charts presented herein may be implemented in a computer-readable medium that includes instructions for causing a programmable processor to carry out the methods described. A "computer-readable medium" includes but is not limited to any volatile or non-volatile media, such as a RAM, ROM, CD-ROM, NVRAM, EEPROM, flash memory, and the like. The instructions may be implemented as one or more software modules, which may be executed by themselves or in combination with other software.

At block 102, a first pacing site within a given heart chamber is selected, which may be an LV pacing site. For the sake of illustration, the methods for selecting multiple pacing sites are presented in the context of selecting multiple pacing sites along the LV for CRT therapy. However, the methods described may be altered or adapted as appropriate for selecting pacing sites in a different heart chamber and/or for use in a different pacing therapy.

The selection of the first pacing site at block 102 may be based on a variety of measurements or be a nominal pacing site. For example, the first pacing site may be selected as the electrode site corresponding to a late activation time of the LV during no LV pacing. An LV activation time is the time interval measured from a reference time point to a sensed R-wave at the pace/sense electrode site. The reference time point may be an atrial sensed or paced event, an R-wave sensed in the RV or a fiducial point identified on a QRS complex sensed in the RV.

A late activation is an activation that occurs relatively later than activation (myocardial depolarization) at other possible LV pace/sense electrode locations. A late activation is not necessarily the latest LV activation that can be measured in the LV since prolonged activation may be associated with pathological or diseased tissue such as myocardial scar tissue, which would be undesirable as a pacing site.

In CRT, the greatest therapeutic benefit may be achieved when the LV is paced at or near a location associated with late intrinsic activation time of the ventricle. To determine an electrode site corresponding to late activation, LV activation times are measured at each of the available LV electrodes relative to a reference time point, such as a sensed R-wave in the RV when no ventricular pacing is delivered. In one embodiment, the LV activation times are measured by sensing for an LV depolarization wavefront (R-wave) at each of the LV electrodes 30, 32, 34 and 36 used as sensing electrodes. LV activation times may be measured during an intrinsic rhythm or during atrial pacing. Typically pacing in the RV will be withheld to obtain the LV activation time measurements during intrinsic ventricular conduction.

In other embodiments, the first pacing site may be selected using other measurements or techniques, which may or may not be combined with measuring LV activation times. For example, hemodynamic measurements may be performed to determine which pacing site results in the greatest hemodynamic benefit. Hemodynamic measurements may be obtained from other physiological sensors 70 coupled to IMD 10 or using clinical techniques such as Doppler echocardiography, fluoroscopy, or LV catheterization.

A second pacing site is selected at block 104. A second pacing site may be selected using any of the measurements discussed in the foregoing. In one embodiment, the second pacing site is selected as a site at which a late activation time is measured during LV pacing at the first pacing site. A method for selecting the second pacing site will be described in greater detail in conjunction with FIG. 4.

At block 106, a capture threshold at each of the first and second pacing sites is measured. The capture threshold generally corresponds to cathodal capture at the selected pacing sites. In some cases however, anodal capture may occur at a lower pacing pulse energy than cathodal capture, simultaneously with cathodal capture, or within a safety pacing margin of the cathodal capture. At decision block 108, a capture analysis algorithm is performed to determine if anodal capture is detected during bipolar pacing using a bipolar combination of the first and second pacing sites. This determination may be made during a capture threshold test, during pacing at a selected pacing pulse energy based on a measured capture threshold and safety pacing margin, or during pacing at any selected pacing energy, which may be a nominal setting or a highest acceptable pacing pulse amplitude or pacing pulse width.

Detection of anodal capture may be performed when using the electrode at the first site as a cathode and the electrode at the second site as an anode and/or a bipole of the opposite polarity, i.e. the first pacing site electrode is an anode and the second pacing site is a cathode. Additional details regarding detecting the presence of anodal capture are described below in conjunction with FIG. 5.

A pacing vector configuration for delivering the multi-site pacing is selected at block 114. If anodal capture is not detected, multi-site pacing can be delivered using the selected first and second pacing site electrodes in two separate pacing vectors. The electrodes at the pacing sites are selected by the IMD switching circuitry 58 as pacing cathodes and any other available electrodes may be selected as an anode, which may be a shared anode or two separate anodes. The selected anode may be away from the left ventricle, to provide a unipolar pacing vector, such as the RV coil electrode or the IMD housing electrode. If the selected anode electrode is positioned along the LV to provide pacing using a bipolar pacing vector, the selected anode is an anode that is verified to not result in anodal capture. For example two LV bipoles may be selected, each having one of the first and second selected electrode sites as the cathode electrode and another LV electrode at a non-selected site as an anode. In another example, one of the selected pacing site electrodes may serve as both an anode in one pacing vector and as a cathode in the second pacing vector. To illustrate with reference to FIG. 1, if LV electrodes 30 and 34 are selected as the first and second pacing sites, electrodes 30 and 34 may be selected as the cathode and anode respectively in a bipolar pacing vector to pace at the site of electrode 30. Electrode 34 may be selected as a cathode paired with RV coil 24 as an anode in a unipolar pacing vector to pace at the site of electrode 34.

If anodal capture is detected at block 108, anodal capture thresholds are measured at one or both of the first and second pacing sites at block 110. Additional details regarding measuring anodal capture thresholds will be described in conjunction with FIG. 5.

If anodal capture is occurring at one of the first and second pacing sites during cathodal pacing at the other of the first and second sites, dual site pacing may be achieved in an energy efficient manner at the two sites using only a single bipole. Dual site pacing may be delivered using the first and second pacing site electrodes as a bipolar pair at a pacing pulse energy that is higher than the higher of the cathodal and anodal pacing thresholds.

In some embodiments, relative battery longevity calculations may be made at block 112 comparing two or more different pacing configurations that include pacing at the two selected pacing sites. For example, after measuring the cathodal capture threshold at the first and second pacing sites, and determining an anodal capture threshold for at least one of the sites, relative battery longevity calculations may be performed to determine the battery expenditure required to pace at the two sites using two different pacing vectors including each of the first and second site electrodes as cathodes versus using a only a single bipole that achieves simultaneous anodal and cathodal capture at the first and second pacing sites.

At block 114, the pacing configuration that results in capture at both pacing sites with the least energy expenditure, i.e. greatest predicted battery longevity, can be selected automatically or displayed to a clinician as a recommended pacing configuration. Capture analysis data and activation times may be transmitted to an external programmer 90 and presented to a clinician, allowing the clinician to make an informed selection of a pacing configuration at block 114. The selected pacing configuration would then be programmed using programmer 90.

Selecting a pacing configuration at block 114 can include selecting a recommended pacing configuration based on activation time measurements and/or anodal capture detection and transmitting the recommended configuration to programmer 170. The clinician may then program a final pacing configuration using this information. Selecting the pacing configuration at block 114 may additionally or alternatively include automatic programming of the selected pacing configuration and delivery of the pacing therapy using the selected configuration.

Figure 4:
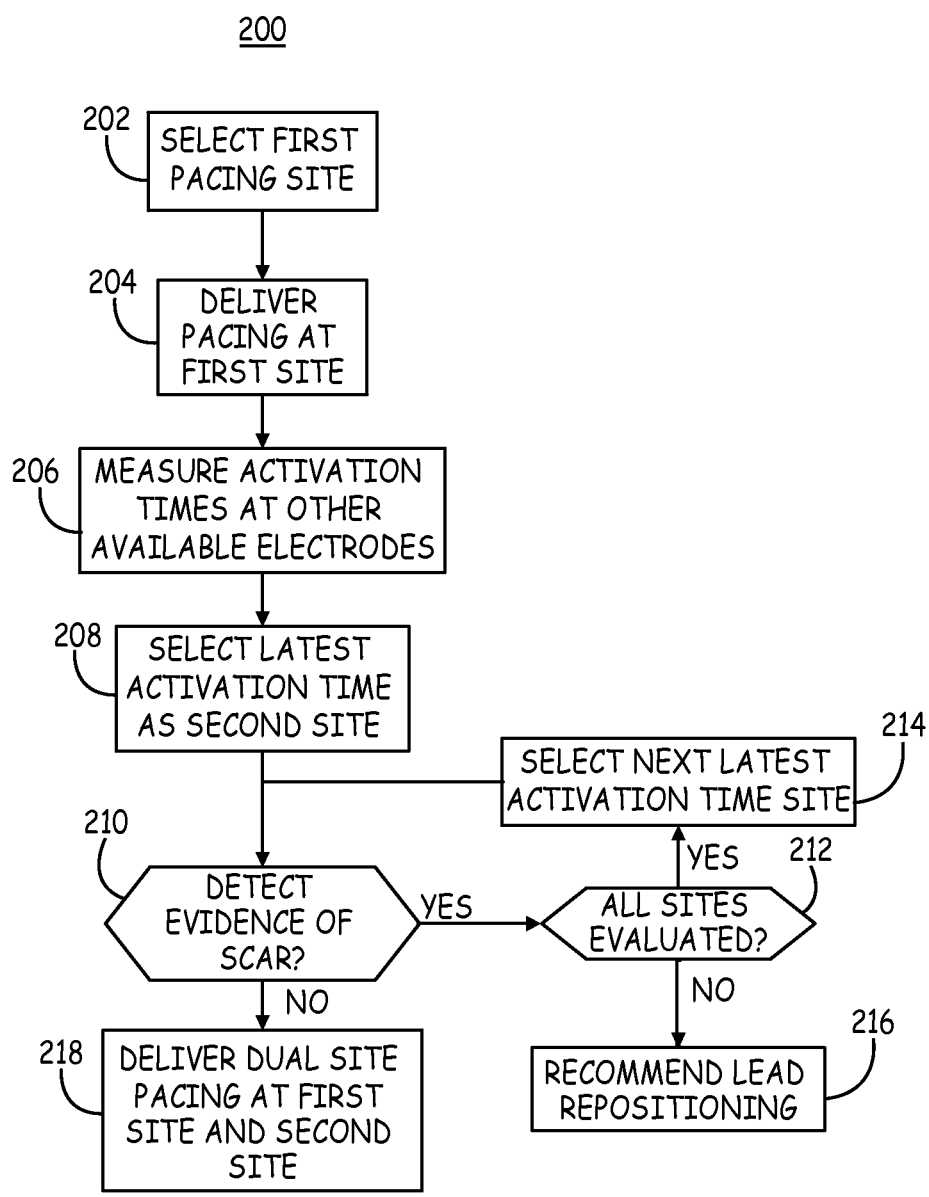
FIG. 4 is a flow chart of one method for selecting a second pacing site for multi-site pacing in a heart chamber according to one embodiment.

FIG. 4 is a flow chart 200 of one method for selecting a second pacing site for multi-site pacing along a heart chamber according to one embodiment. At block 202, the first pacing site is selected using any of the methods described above. The first pacing site may be selected based on a hemodynamic measurement, site of late activation or other factors, such as capture threshold and lead impedance, or may even be a nominal pacing site. Once the first pacing site is selected, pacing is delivered at the first site at block 204.

During pacing at the first site, activation times at other available electrode sites are measured at block 206. For example, the electrodes 30, 32, 34, and 36 shown in FIG. 1 can be referred to as LV1, LV2, LV3 and LV4 respectively. If the first pacing site is LV1, pacing is delivered using the LV1 electrode paired with any of the other electrodes 32, 34 or 36 for bipolar pacing or with an electrode positioned away from the LV for unipolar pacing, such as housing electrode 12. The other LV electrodes 32, 34 and 36 are used for sensing a conducted depolarization signal, i.e. R-wave, arising from the pacing evoked response at the LV1 electrode. A time interval from a reference time point to the sensed R-wave at each of the other LV electrodes 32, 34 and 36 is measured as the respective activation time for the given electrode.

The time interval may be measured from the LV pacing pulse, from a sensed R-wave, or from an atrial paced or sensed event. The electrode site corresponding to the latest activation time following the LV pacing pulse at the first pacing site is selected as the second pacing site at block 208. Sometimes, the latest activation site may be in scar tissue or ischemic tissue and is therefore not a desired pacing site. As such, in some embodiments, additional EGM signal analysis may be performed at block 210 to verify that the latest activation site is not associated with necrotic, ischemic or other pathological tissue that is deemed undesirable as a pacing site.

Detection for the evidence of scar tissue or ischemia could include measurement of a high pacing capture threshold at that site, observation of delayed exit of a pacing-induced evoked response from that site (i.e., delayed initiation of QRS complex from the pacing pulse), or by observation of a small QRS complex or fractionated QRS complex in the EGM obtained using a short sensing bipole including the candidate pacing site electrode. A small or fractionated QRS complex would be identified from the EGM signal obtained using the electrode at the pacing site when pacing is not delivered at that site, i.e., either during intrinsic rhythm or possibly during pacing at a distant site.

A delayed or altered QRS complex as evidence of scar or ischemic tissue detected at block 210 would result in rejection of the site having the latest activation time as a pacing site. If other pacing sites are still available, as determined at block 212, the electrode site having the next latest activation time is selected at block 214. This site may also be evaluated for any pathological abnormalities of the QRS or high capture threshold that would indicate an undesirable pacing site at block 210.

If all pacing sites are evaluated without identifying a late activation site that is not associated with scar or ischemic tissue, a recommendation to replace or reposition the lead may be issued at block 216. Alternatively, the clinician may accept pacing at the single first site.

If a second site characterized by relatively late activation without evidence of scar or ischemia is identified at block 210, dual site pacing is delivered in the LV at block 218 using the first site and the second site. This dual site pacing may be delivered using two different bipoles that include electrodes positioned at the first and second selected sites and a different electrode as a shared anode or two separate anodes. Dual site pacing could alternatively be delivered wherein one or both of the selected pacing sites are paced using a unipolar combination that includes an electrode at the selected pacing site and an electrode positioned away from the LV, such as an RV ring electrode, RV coil electrode, or housing electrode.

In some embodiments, the dual site pacing may be delivered at block 218 at the two selected sites using a single bipole. The pacing pulse energy is adjusted to cause cathodal capture at one of the selected sites and anodal capture at the other of the selected sites. In this way, energy efficient dual site pacing is achieved at two desired pacing sites by delivering a single bipolar pacing pulse.

While selection of two pacing sites is described in illustrative examples presented herein, it is contemplated that the methods could be extended to additional pacing sites. For example, once two pacing sites are selected, a third site, fourth site, and so on could be selected based on additional activation times measured during pacing at all previously selected sites.

It is contemplated that automatic programming of the selected sites for delivering dual site pacing may be implemented in the IMD. Alternatively, selection of the dual site pacing configuration at block 218 may involve first issuing a recommended configuration based on the activation times then allowing a clinician to program the recommended configuration or selecting a different configuration using the LV activation times measured at secondary sites during LV pacing at a first site.

Figure 5:
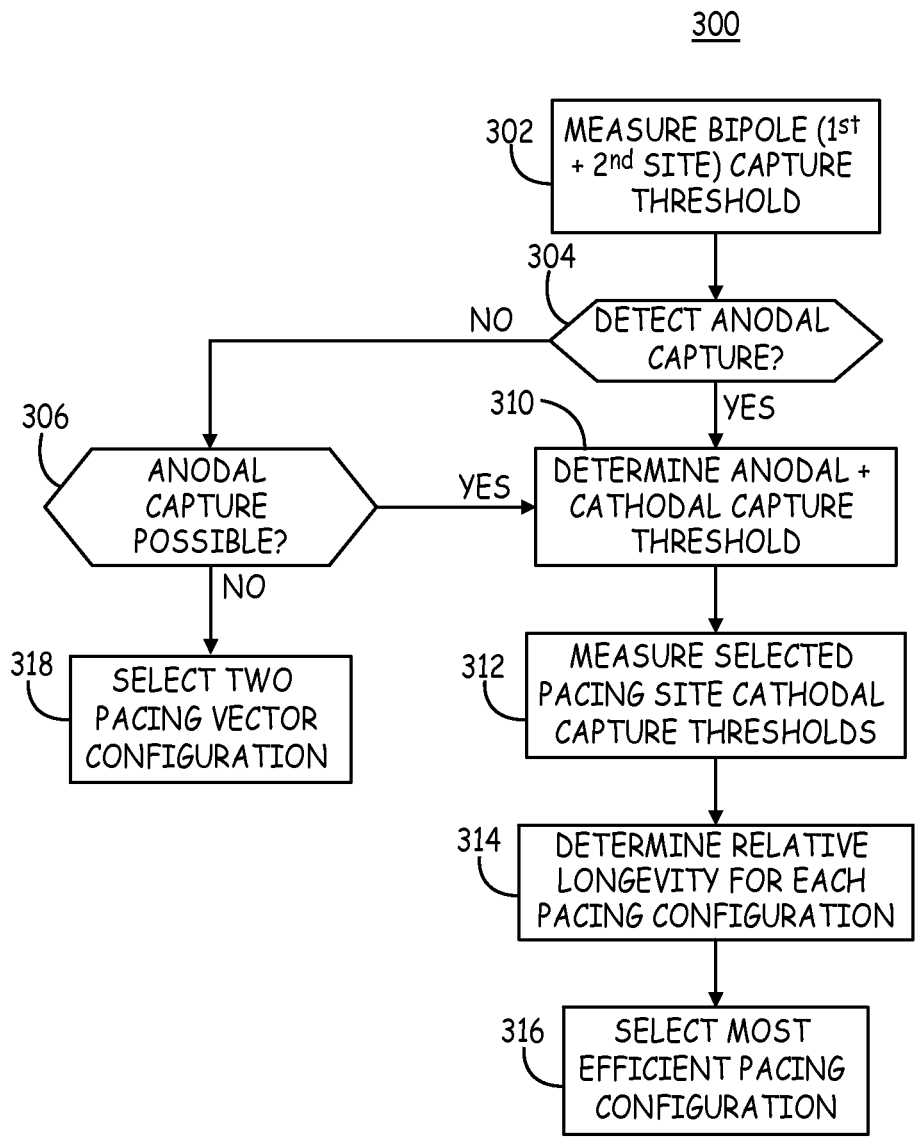
FIG. 5 is a flow chart of a method for selecting a pacing configuration for dual site pacing in a heart chamber according to one embodiment.

FIG. 5 is a flow chart 300 of a method for selecting a pacing configuration for dual site pacing of a heart chamber according to one embodiment. The first and second pacing sites for the dual site pacing are previously selected, for example according to the methods described in FIG. 4, according to clinician preference, or may be default electrode locations.

At block 302, a capture threshold test is performed for a single bipole defined by the previously selected first and second pacing sites. During the capture threshold test, the capture analysis module determines whether anodal capture is present at block 304. A capture threshold test may be performed according to any implemented method. For example, an evoked response, a conducted depolarization associated with a delivered pacing pulse or other evidence of pacing capture may be sensed or measured while adjusting the pacing pulse energy until the evidence of capture disappears and/or reappears for determining the lowest pacing pulse energy that captures the myocardium.

In one embodiment, the pacing pulse is delivered in the LV and an EGM signal sensed in the RV or another distant bipole is used to determine whether capture has occurred. For example, an intrinsic conduction time to an RV sensing electrode bipole may be measured and compared to a conduction time measured by the RV sensing bipole during LV pacing at different pacing pulse energies. The conduction time is compared to the intrinsic conduction time to identify when a change in conduction time occurs due to capture of the LV pacing pulse.

The presence of anodal capture during the capture threshold test may be determined using the methods generally disclosed in commonly-assigned U.S. patent application Ser. No. 13/192,713, hereby incorporated herein by reference in its entirety. For example, anodal capture may be detected during a capture threshold test by determining a capture threshold for a bipole including the first pacing site electrode as a cathode electrode and a second LV electrode as the anode. Then, using the first pacing site as a cathode in a unipolar pacing combination, determining the unipolar capture threshold. If the unipolar capture threshold is greater than the bipolar capture threshold, anodal capture is likely present.

This may be further verified by switching the second LV electrode used as an anode to a cathode polarity and determining the unipolar capture threshold for the second LV electrode. If this capture threshold is closer to the bipole capture threshold than the unipolar capture threshold for the first pacing site electrode, anodal capture is likely present during bipolar pacing using the first and second electrodes.

Other measurements such as evoked response timing and/or EGM signal morphology may be made for detecting anodal capture as described in the above-incorporated '713 application. Comparing measured responses to a pacing bipole including the first pacing site electrode as a cathode and the second pacing site electrode as the anode to measured responses to a pacing unipole using the first pacing site electrode as a cathode and a pacing unipole using the second pacing site electrode as a cathode allows detection and discrimination of anodal capture during bipolar pacing using the two pacing sites. Measurements for the bipole that are closest to measurements associated with the unipole using the second pacing site electrode as a cathode are evidence of anodal capture during bipolar pacing.

Detection of anodal capture at block 304 may be determined for both polarity configurations of the single bipole, i.e. the first electrode as the cathode and the second electrodes as the anode and the opposite polar assignments of the first electrode as the anode and the second electrode as the cathode. If anodal capture is detected during the capture threshold test for either polarity of the bipole, a threshold for simultaneous anodal and cathodal capture is determined at block 310. The anodal capture threshold may be less than, equal to, or greater than the cathodal capture. Simultaneous capture may be determined, for example, by adjusting the pacing pulse energy until an evoked response measured at both the anode and the cathode occurs approximately simultaneously. Either the pulse amplitude and/or the pulse width may be adjusted during capture threshold tests to allow an amplitude threshold for a fixed pulse width and/or a pulse width threshold for a fixed pulse amplitude to be determined.

If anodal capture is not detected during a capture threshold test for either polarity assignments of the bipole at block 304, additional testing may be performed at block 306 to determine if anodal capture is possible at higher pacing pulse energies using a bipole defined by the two pacing site electrodes. The pacing pulse energy delivered by the bipole may be increased at block 306 until anodal capture is detected. If anodal capture is not detected or occurs at a pacing pulse energy considered to be too high to be acceptable, e.g. causing excessive battery drain that reduces battery longevity by more than a given number of weeks, months or years, the polarity of the bipole may be switched and the test repeated to determine if anodal capture is achieved with the opposite polarity.

If anodal capture is not achieved using a bipole defined by the two pacing site electrodes, a multi-site pacing configuration is selected at block 318 that includes two pacing vectors for delivering pacing at the two selected pacing sites. Each of the first pacing site electrode and the second pacing site electrode are selected as cathodes and paired with a respective anode, which may be a shared anode or separate anodes. In practice, dual site pacing of the two selected sites may be achieved by using two unipolar pacing vectors, two bipolar pacing vectors, or a combination of a unipolar and a bipolar pacing vector, each vector including one of the selected pacing sites as the cathode electrode along the LV paired with an anode that does not result in anodal stimulation.

If anodal capture is possible at a higher pacing pulse energy, but within a range of acceptable pacing pulse energies, as determined at block 306, the capture threshold for simultaneous anodal and cathodal capture is determined at block 310. This simultaneous anodal plus cathodal capture threshold will be used to compare the energy expenditure of dual site pacing delivered using a single bipole to the energy expenditure for delivering dual site pacing using two pacing vectors. A maximum acceptable pacing pulse energy may be based on the measured cathodal capture threshold or may be a previously established maximum pulse amplitude or pulse width. For example, if cathodal capture is possible at a relatively low pacing output, such as 1 V, anodal capture may be possible at a significantly higher pacing output but at too high of energy cost. As such, even though anodal capture may be possible, it may be rejected based on an established maximum pacing pulse output at block 306. Two pacing vectors are selected at block 318 for pacing the two selected sites.

If anodal capture is possible at block 306, the capture thresholds are measured at block 312 for each of the first and second pacing sites selected as cathodes in pacing vectors different than the bipole defined by the first and second pacing site electrodes. These capture thresholds are measured using the selected cathode electrode paired with an anode that does not include the selected pacing sites. The cathodal capture thresholds measured for the first and second pacing sites using different pacing vectors and the capture threshold for dual site simultaneous anodal and cathodal capture measured at block 310 are used to compute relative battery expenditure or longevity estimates for two different pacing configurations at block 314.

The expected battery longevity is computed for at least two pacing configurations: 1) two different pacing vectors each using one of the selected pacing site electrodes as a cathode to achieve cathodal capture at the two sites and 2) a single bipole defined by the two selected pacing site electrodes to achieve simultaneous anodal and cathodal capture at the two sites. Battery longevity may be computed for additional pacing configurations such as the reversed polarity of the single bipole defined by the two selected pacing sites and for different pacing vector configurations that include the first and second pacing site electrodes selected as cathodes paired with different candidate anodes that do not result in anodal stimulation. Lead impedance measurements and capture thresholds corresponding to these two (or more) possible pacing configurations are used to compute relative battery longevity, with other pacing control parameters equal, such as expected pacing frequency and safety pacing margin.

Computing estimated battery longevity or battery expenditure is one method for establishing a threshold or maximum acceptable pacing pulse output for selecting a single bipole as the pacing configuration for dual site pacing. If the pacing pulse output required for simultaneous cathodal and anodal capture results in a higher estimated battery expenditure than the battery expenditure required to deliver dual site pacing using two different pacing vectors, the pacing pulse output for single bipole, dual-site pacing is considered too high.

The pacing configuration resulting in the most energy efficient pacing, i.e. lowest estimated battery expenditure or longest predicted battery longevity, is automatically selected or recommended to a clinician via programmer 90 at block 316 as the dual site pacing configuration. In some cases, the simultaneous anodal plus cathodal capture threshold is low enough that energy efficient pacing can be delivered to two sites using a single bipole. In other cases, the threshold for achieving simultaneous anodal and cathodal capture may be so high that dual site pacing using two pacing vectors, two bipolar, two unipolar or a combination of both, may be more energy efficient.

It is further contemplated that additional pacing sites may be selected in a multi-site pacing therapy such that an overall pacing configuration of a given heart chamber may include a single bipole delivering pacing at two sites simultaneously and one or more additional pacing vectors to pace at one or more additional pacing sites along the same heart chamber.

Figure 6:
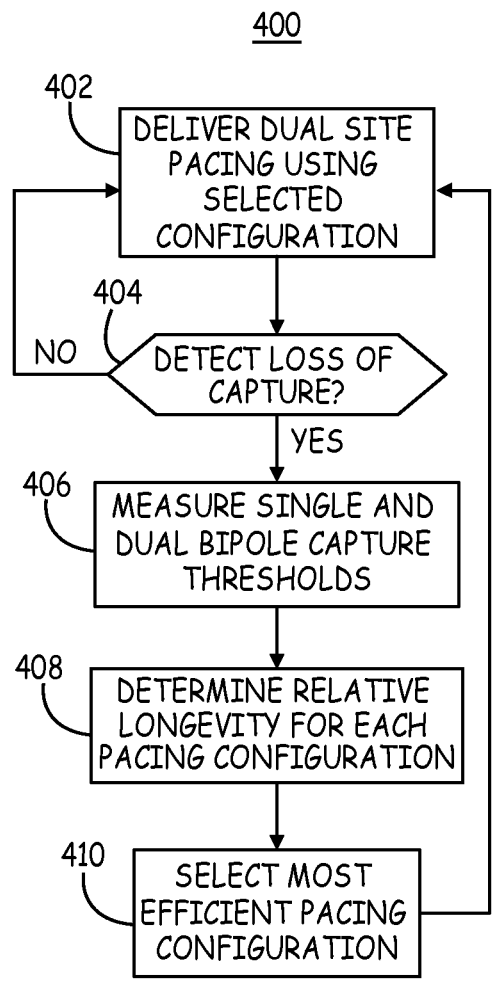
FIG. 6 is a flow chart of a method for controlling multi-site pacing according to one embodiment.

FIG. 6 is a flow chart 400 of a method for controlling multi-site pacing according to one embodiment. At block 402, dual-site pacing pulses are delivered in a single heart chamber using a selected pacing configuration. The pacing configuration is selected using the methods described in conjunction with FIGS. 4 and 5 above. Other heart chambers may or may not be paced during dual site pacing in the one heart chamber.

During pacing, loss of capture detection algorithms may be executed, continuously or periodically, at block 404 to detect loss of capture in the heart chamber being paced at multiple sites. Loss of capture detection may involve measuring evoked responses, measuring conduction times, EGM signal morphology analysis, or performing capture threshold tests. If the selected pacing configuration is dual site pacing using a single bipole, the loss of capture detection performed at block 404 may include detecting the presence (or absence) of anodal capture. Anodal capture may be detected based on an evoked response time interval or QRS signal morphology obtained at the anode electrode.

If loss of capture has occurred, a capture threshold test is performed at block 406. In some embodiments, loss of capture monitoring may not be performed on a continuous basis at block 404. In that case, periodic capture threshold tests may be performed at block 406 with or without waiting for a loss of capture detection. As such, in some embodiments, block 404 may be omitted and periodic capture threshold tests are performed instead. Alternatively, other monitoring may be performed that trigger a capture threshold test, such as monitoring of hemodynamic signals, pulmonary edema, or other signs of a worsening of heart failure that may be caused by a loss of capture and associated lack of therapeutic benefit of the pacing therapy.

The capture threshold test performed at block 406 includes measuring capture thresholds for at least the following pacing vectors: 1) a bipole defined by the first pacing site and the second pacing site and 2) the anode of the bipole defined by the first and second pacing site switched to a cathode polarity and paired with any anode. Additional vectors using the cathode of the bipole defined by the first pacing site and the second pacing site paired with any anode and/or the opposite polarity of the bipole defined by the first and second pacing site (switched pole assignments) tested to determine the capture thresholds for each pacing vector.

At block 408, relative battery longevity computations are made to compare at least two different possible pacing configurations. The energy expenditure is computed for at least: 1) a single bipole configuration which includes both the first and second selected pacing site electrodes, and 2) a dual pacing vector configuration that includes one bipolar or unipolar vector using the first pacing site electrode as the cathode and another bipolar or unipolar vector using the second pacing site electrode as the cathode. The battery longevity estimate may be computed for additional pacing configurations which include using the first and second pacing site electrodes as cathodes in any unipolar or bipolar pacing vectors.

At block 410, the pacing configuration that allows capture at both the first and second electrode sites with the greatest battery longevity estimate is automatically selected as the pacing configuration. In this way, after an initial pacing configuration is selected for multi-site pacing, if changes in capture thresholds occur, the pacing site configuration may be automatically adjusted by the IMD to a new configuration that is more energy efficient and still provides capture at the selected pacing sites.

In the flow charts presented herein, it is recognized that all blocks shown may not be performed in some embodiments or may be performed in a different order than the order shown. Furthermore, operations described in conjunction with separate flow charts presented herein may be combined in any combination to successfully achieve the result of selecting multiple pacing sites along a heart chamber and selecting an energy efficient manner for delivering the multi-site pacing.

Thus, an apparatus and method for controlling multi-site pacing have been presented in the foregoing description with reference to specific embodiments. It is appreciated that various modifications to the referenced embodiments may be made without departing from the scope of the disclosure as set forth in the following claims.

The invention claimed is:

1. A method for controlling a multi-site pacing therapy, the method comprising:
   selecting a first electrode positioned at a first pacing site along a first heart chamber;
   selecting a second electrode positioned at a second pacing site along the first heart chamber;
   delivering pacing pulses to the first heart chamber using a bipole comprising the first electrode and the second electrode;
   determining whether anodal and cathodal capture can be achieved during pacing using the bipole; and
   selecting a multi-site pacing configuration comprising the bipole for singly pacing the first and second pacing sites in response to anodal and cathodal capture being achieved.

2. The method of claim 1, wherein determining whether anodal and cathodal capture can be achieved comprises establishing a maximum acceptable pacing pulse output for achieving anodal and cathodal capture during pacing using the bipole and determining if anodal and cathodal capture can be achieved during pacing using the bipole at a pacing pulse output that does not exceed the maximum acceptable pacing pulse output.

3. The method of claim 2, wherein establishing the maximum acceptable pacing pulse output comprises:
   determining a cathodal capture threshold for one of the first electrode and the second electrode; and
   setting the acceptable maximum pacing pulse output limit in response to the cathodal capture threshold.

4. The method of claim 1, wherein determining whether anodal and cathodal capture can be achieved comprises determining a conduction time to a distant sensing bipole in response to bipolar pacing using the bipole and at least one of unipolar pacing using the first electrode and unipolar pacing using the second electrode.

5. The method of claim 1, wherein determining whether anodal and cathodal capture can be achieved comprises determinng one of an evoked response and a cardiac signal morphology.

6. The method of claim 1, further comprising:
   determining an anodal capture threshold for at least one of the first electrode and second electrode;
   determining a cathodal capture threshold for at least one of the first electrode and the second electrode; and
   setting a pacing pulse energy at a safety pacing margin above a higher one of the anodal capture threshold and the cathodal capture threshold.

7. The method of claim 1, further comprising:
   determining an anodal capture threshold for at least one of the first electrode and the second electrode;
   determining a cathodal capture threshold for each of the first electrode and the second electrode;

computing a first estimated battery expenditure for pacing at the first site and the second site using only the bipole; and computing a second estimated battery expenditure for pacing the first site and the second site using two pacing vectors comprising the first electrode and second electrode selected as cathode electrodes;

wherein determining whether anodal and cathodal capture can be achieved during pacing using the bipole comprises verifying that the first energy expenditure does not exceed the second energy expenditure.

8. The method of claim 1, further comprising:
performing a capture threshold test; and
selecting a different pacing configuration in response to a change in a capture threshold at one of the first pacing site and the second pacing site.

9. The method of claim 8, further comprising:
monitoring for loss of capture during pacing using the bipole; and
performing the capture threshold test in response to detecting the loss of capture.

10. The method of claim 1, wherein delivering the multi-site therapy comprises delivering cardiac resynchronization therapy, wherein the first site and the second site are located along the left ventricle.

11. A medical device for delivering a multi-site pacing therapy, comprising:
a plurality of electrodes to sense cardiac signals and deliver cardiac pacing pulses;
a therapy delivery module to deliver cardiac pacing pulses to a patient's heart via the plurality of electrodes;
a sensing module to sense cardiac signals; and
a controller configured to:
select a first electrode positioned at a first pacing site along a first heart chamber;
select a second electrode positioned at a second pacing site along the first heart chamber;
control the therapy delivery module to deliver pacing pulses to the first heart chamber using a bipole comprising the first electrode and the second electrode;
determine, in response to the sensed cardiac signals, whether anodal and cathodal capture can be achieved during pacing using the bipole; and
selecting a multi-site pacing configuration comprising the bipole for singly pacing the first and second pacing sites in response to anodal and cathodal capture being achieved.

12. The device of claim 11, wherein the controller is configured to determine whether anodal and cathodal capture can be achieved by establishing a maximum acceptable pacing pulse output for achieving anodal and cathodal capture during pacing using the bipole, and determining whether anodal and cathodal capture can be achieved during pacing using the bipole at a pacing pulse output that does not exceed the maximum acceptable pacing pulse output.

13. The device of claim 12, wherein establishing the acceptable maximum pacing pulse output comprises:
determining a cathodal capture threshold for one of the first electrode and the second electrode; and
setting the acceptable maximum pacing pulse output using the cathodal capture threshold.

14. The device of claim 11, wherein determining whether anodal and cathodal capture can be achieved comprises determining an inter-chamber conduction time to a distant sensing bipole in response to bipolar pacing using the bipole and at least one of unipolar pacing using the first electrode and unipolar pacing using the second electrode.

15. The device of claim 11, wherein determining whether anodal and cathodal capture can be achieved comprises determining one of an evoked response and a cardiac signal morphology.

16. The device of claim 11, wherein the controller is further configured to:
determine an anodal capture threshold for at least one of the first electrode and second electrode;
determine a cathodal capture threshold for at least one of the first electrode and the second electrode; and
set a pacing pulse energy at a safety pacing margin above a higher one of the anodal capture threshold and the cathodal capture threshold.

17. The device of claim 11, wherein the controller is further configured to:
determine an anodal capture threshold for at least one of the first electrode and the second electrode;
determine a cathodal capture threshold for each of the first electrode and the second electrode;
compute a first estimated battery expenditure for pacing at the first site and the second site using only the bipole;
compute a second estimated battery expenditure for pacing the first site and the second site using two pacing vectors comprising the first electrode and second electrode selected as cathode electrodes; and
determine whether anodal and cathodal capture can be achieved during pacing using the bipole by verifying that the first energy expenditure does not exceed the second energy expenditure.

18. The device of claim 11, wherein the controller is further configured to:
perform a capture threshold test; and
select a different pacing configuration in response to a change in a capture threshold at one of the first pacing site and the second pacing site.

19. The device of claim 18, wherein the controller is further configured to:
monitor for loss of capture during pacing using the bipole; and
perform the capture threshold test in response to detecting the loss of capture.

20. The device of claim 11, wherein the first site and the second site are located along the left ventricle.

21. A non-transitory computer-readable medium storing a set of instructions which when implemented in a medical device cause the device to perform a method for controlling a multi-site pacing therapy, the method comprising:
selecting a first electrode positioned at a first pacing site along a first heart chamber;
selecting a second electrode positioned at a second pacing site along the first heart chamber;
delivering pacing pulses to the first heart chamber using a bipole comprising the first electrode and the second electrode;
determining whether anodal and cathodal capture can be achieved during pacing using the bipole; and
selecting a multi-site pacing configuration comprising the bipole for singly pacing the first and second pacing sites in responve to anodal and cathodal capture being achieved.

* * * * *